United States Patent
Chen et al.

(10) Patent No.: US 7,172,907 B2
(45) Date of Patent: Feb. 6, 2007

(54) **CYANINE DYE LABELLING REAGENTS WITH *MESO*-SUBSTITUTION**

(75) Inventors: Chung-Yuan Chen, Piscataway, NJ (US); Shiv Kumar, Belle Mead, NJ (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 283 days.

(21) Appl. No.: 10/394,108

(22) Filed: Mar. 21, 2003

(65) Prior Publication Data
US 2004/0186278 A1    Sep. 23, 2004

(51) Int. Cl.
G01N 33/533 (2006.01)
C07K 17/02 (2006.01)
C07D 413/06 (2006.01)
C07D 417/06 (2006.01)
C07D 403/06 (2006.01)

(52) U.S. Cl. .......................... 436/546; 435/6; 435/7.5; 435/188; 436/501; 530/391.3; 530/391.5; 548/156; 548/219; 548/455

(58) Field of Classification Search ................ 436/546, 436/501; 435/6, 7.5, 188; 530/391.3, 391.5; 548/455, 156, 219
See application file for complete search history.

(56) References Cited

U.S. PATENT DOCUMENTS

| | | | |
|---|---|---|---|
| 6,004,536 A * | 12/1999 | Leung et al. | 424/9.6 |
| 6,048,982 A * | 4/2000 | Waggoner | 548/148 |
| 6,733,744 B1 * | 5/2004 | Achilefu et al. | 424/9.6 |
| 2002/0025491 A1* | 2/2002 | Morishima et al. | 430/270.19 |
| 2002/0064794 A1* | 5/2002 | Leung et al. | 435/6 |
| 2002/0156288 A1* | 10/2002 | Caputo et al. | 548/156 |

FOREIGN PATENT DOCUMENTS

| | | |
|---|---|---|
| DE | 19 957007 A1 * | 5/2001 |
| JP | 09230539 A1 * | 9/1997 |
| WO | WO 01/177229 A2 * | 10/2001 |

* cited by examiner

Primary Examiner—Mary E. Ceperley
(74) Attorney, Agent, or Firm—Yonggang Ji

(57) ABSTRACT

Disclosed are cyanine dyes having meso-substituents in the polymethine chain linking the heterocyclic ring systems. The dyes are of formula (1):

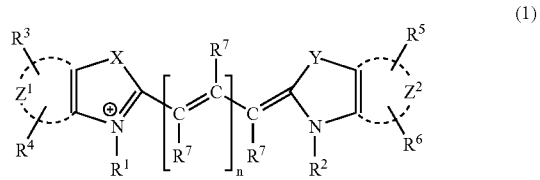

in which groups $R^3$ and $R^4$ are attached to the $Z^1$ ring structure and groups $R^5$ and $R^6$ are attached to the $Z^2$ ring structure, and n=1, 2 or 3; $Z^1$ and $Z^2$ independently represent the atoms necessary to complete one ring, or two fused ring aromatic or heteroaromatic systems, each ring having five or six atoms selected from carbon atoms and optionally no more than two atoms selected from oxygen, nitrogen and sulphur; X and Y are the same or different and are selected from oxygen, sulphur, —CH═CH— and the group:

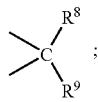

at least one of groups $R^1$, $R^2$, $R^3$, $R^4$, $R^5$, $R^6$ (and $R^8$ and $R^9$ if present) is the group -E-F where E is a spacer group and F is a target bonding group; one of groups $R^7$ is selected from —CN, —Cl, —F, —CF$_3$ and —C(O)R$^{10}$ wherein $R^{10}$ is selected from H, $C_1$–$C_6$ alkyl and aryl. Preferred group $R^7$ is meso-substituted —CN, which confers an unexpected hypsochromic shift of approximately 40 nm in the emission spectrum, when compared with the corresponding unsubstituted analogue. The dyes are useful for labelling and detecting a variety of target molecules.

20 Claims, 2 Drawing Sheets

Absorption (———) and Emission (— — —) Spectra of 2-{5-[1-(5-Carboxypentyl)-3,3-dimethyl-1,3-dihydro-2H-indol-2-ylidene]-3-cyano-1,3-pentadienyl}-1,3,3-trimethyl-3H-indolinium (Methanol)

Reaction Scheme illustrating the Conjugation of 2-{5-[1-(5-Carboxypentyl)-3,3-dimethyl-1,3-dihydro-2H-indol-2-ylidene]-3-cyano-1,3-pentadienyl}-1,3,3-trimethyl-3H-indolinium with Dideoxyuridine-5'-triphosphate

CYANINE DYE LABELLING REAGENTS WITH *MESO*-SUBSTITUTION

BACKGROUND OF INVENTION

The present invention relates to the field of labelling reagents. In particular, the invention relates to cyanine dyes having meso-substituents in the polymethine chain linking the heterocyclic systems. The invention also relates to assay methods utilising such dyes.

There is increasing interest in, and demand for, fluorescent reporters for use in the labelling and detection of biomolecules. Cyanine and related dyes offer a number of advantages over other fluorescent dye reagents and they are finding widespread use as fluorescent labels in such diverse areas as sequencing, microarrays, flow cytometry and proteomics. The cyanine dyes are characterised by having very high extinction coefficients and favourable quantum yields. In addition, cyanine dyes possess good photostability and are not photobleached. The dyes have been used extensively as labels in biological studies.

U.S. Pat. No. 6,048,982 (Waggoner, A. S.) discloses luminescent cyanine dyes having the structure:

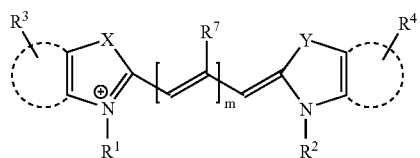

wherein X and Y are independently selected from the group consisting of O, S and $CH_3$—C—$CH_3$; m is an integer from 1–4 and at least one of the groups $R^1$, $R^2$, $R^3$, $R^4$ and $R^7$ is a reactive group, reactive with amino, sulphydryl or hydroxy nucleophiles.

WO 02/26891 (Molecular Probes Inc.) discloses cyanine dyes incorporating similar structures.

In cyanine dyes of the above formula, the number of methine groups linking the heterocyclic ring systems defines the absorption maxima of the dyes. Thus, the absorption maxima increase from Cy™3 to Cy5 to Cy7 by an increment of approximately 100 nm each as illustrated below. The corresponding emission peaks of Cy3, Cy5 and Cy7 are also separated by approximately 100 nm, as shown in Table 1.

TABLE 1

| Compound | Structure X = Y = C(CH$_3$)$_2$ | Abs max (nm) | Em max (nm) |
|---|---|---|---|
| Cy3 | n = 1 | 550 | 570 |
| Cy5 | n = 2 | 649 | 670 |
| Cy7 | n = 3 | 743 | 767 |

Moreover, the absorption and emission maxima are not much affected by the introduction of either electron withdrawing or donating substitution(s) on the phenyl rings of the heterocycles. Substitution of the phenyl rings with naphthyl rings has been shown to offer the largest bathochromic shifts for the indocyanine dyes giving rise to Cy3.5 and Cy5.5 dyes having spectral characteristics as shown in Table 2.

TABLE 2

| Compound | Structure X = Y = C(CH$_3$)$_2$ | Abs max (nm) | Em max (nm) |
|---|---|---|---|
| Cy3.5 | n = 1 | 581 | 596 |
| Cy5.5 | n = 2 | 675 | 694 |

In many applications that utilise fluorescent dyes, especially for high throughput DNA sequencing, it is desirable to have highly fluorescent, functionalised dyes with absorption maxima (and therefore, emission maxima) having approximately 25 to 30 nm spacing in the entire spectral range from 550 nm to 750 nm. Thus, there is requirement for additional dyes having spectral characteristics that complement those listed above. British Patent No. 620801 (Ilford Ltd) relates to the preparation of cyanine dyestuffs having a meso-substituted cyano group. The spectral properties of the dyes are not disclosed however. Chibisov, A. K. et al (J.Chem-.Soc. Faraday Trans., (1996), 92(24), 4917–25) describe a spectroscopic study involving indocarbocyanines with substituents in the meso position of the polymethine chain. These dyes have not been described for use in the labelling and detection of materials, particularly biological molecules.

SUMMARY OF INVENTION

Accordingly, in a first aspect there is provided a dye of formula (1):

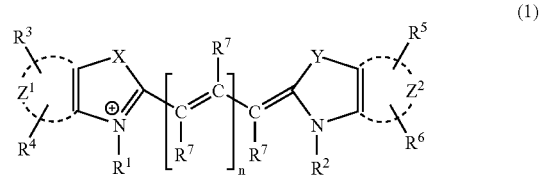

wherein:
groups $R^3$ and $R^4$ are attached to the $Z^1$ ring structure and groups $R^5$ and $R^6$ are attached to the $Z^2$ ring structure, and n=1, 2 or 3;

$Z^1$ and $Z^2$ independently represent the atoms necessary to complete one ring, or two fused ring aromatic or heteroaromatic systems, each ring having five or six atoms selected from carbon atoms and optionally no more than two atoms selected from oxygen, nitrogen and sulphur;

X and Y are the same or different and are selected from oxygen, sulphur, —CH=CH— and the group:

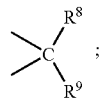

at least one of groups $R^1$, $R^2$, $R^3$, $R^4$, $R^5$, $R^6$ (and $R^8$ and $R^9$ if present) is the group -E-F where E is a spacer group having a chain from 1–20 atoms selected from the group consisting of carbon, nitrogen, oxygen, sulphur and phosphorus atoms and F is a target bonding group;

one of groups $R^7$ is selected from —CN, —Cl, —F, —CF$_3$ and —C(O)$R^{10}$ wherein $R^{10}$ is selected from H, $C_1$–$C_6$ alkyl and aryl;

remaining groups $R^7$ are hydrogen or two of $R^7$ together with the group:

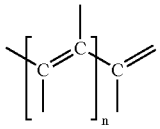

form a hydrocarbon ring system which may optionally contain a heteroatom selected from —O—, —S—, or >NH and n is hereinbefore defined;

when any of groups $R^3$, $R^4$, $R^5$ and $R^6$ is not said group -E-F, said remaining groups $R^3$, $R^4$, $R^5$ and $R^6$ are independently selected from hydrogen, halogen, hydroxyl, amino, mono- or di-$C_1$–$C_4$ alkyl-substituted amino, sulphydryl, nitro, mono- or di-nitro substituted benzyl, carboxyl, $C_1$–$C_6$ alkoxy, $C_1$–$C_6$ alkyl, aryl, heteroaryl, aralkyl, sulphonate, sulphonic acid, quaternary ammonium and the group —$(CH_2)_k$—W;

when any of groups $R^8$ and $R^9$ is not said group -E-F, said remaining groups $R^8$ or $R^9$ are independently selected from $C_1$–$C_4$ alkyl and —$(CH_2)_k$—W;

when any of groups $R^1$ and $R^2$ is not said group -E-F, said remaining groups $R^1$ or $R^2$ are selected from hydrogen, $C_1$–$C_6$ alkyl, benzyl, mono- or di-nitro-substituted benzyl and—$(CH_2)_k$—W;

wherein W is selected from sulphonate, sulphonic acid, quaternary ammonium and carboxyl; and k is an integer from 1 to 6.

Suitably, the dye according to the first aspect includes a counter-ion, for example, trifluoroacetate ($F_3CCO_2^-$), perchlorate ($ClO_4^-$), $Br^-$, or $I^-$, which may serve to balance the formal charge (or charges) on the dye molecule.

In one embodiment according to the first aspect, there is provided a reagent for luminescent detection of a target material wherein said reagent is a fluorescent dye according to formula (1) and wherein groups $R^1$, $R^2$, $R^3$, $R^4$, $R^5$, $R^6$, $R^7$, $Z^1$, $Z^2$, X and Y are hereinbefore defined; with the proviso that none of groups $R^1$, $R^2$, $R^3$, $R^4$, $R^5$ and $R^6$ contains a nitro, or mono- or di-nitro substituted benzyl group.

In a second embodiment according to the first aspect, the dye according to formula (1) is a non-fluorescent or substantially non-fluorescent dye wherein groups $R^1$, $R^2$, $R^3$, $R^4$, $R^5$, $R^6$, $R^7$, $Z^1$, $Z^2$, X and Y are hereinbefore defined and wherein at least one of groups $R^1$, $R^2$, $R^3$, $R^4$, $R^5$ and $R^6$ comprises at least one nitro group. In this embodiment, suitably, the at least one nitro group may be attached directly to the $Z^1$ and/or $Z^2$ ring structures. In the alternative, a mono- or di-nitro-substituted benzyl group may be attached to the $R^1$, $R^2$, $R^3$, $R^4$, $R^5$ or $R^6$ positions and the dye may optionally be further substituted with one or more nitro groups attached directly to the $Z^1$ and/or $Z^2$ ring structures.

Preferably, in the dye according to the first aspect, $R^7$ is selected from meso-substituted —CN, —Cl, —F, —$CF_3$ and —$C(O)R^{10}$ wherein $R^{10}$ is selected from H, $C_1$–$C_6$ alkyl and aryl, and remaining groups $R^7$ are hydrogen.

The term "meso-substituted" is intended to mean that the central $R^7$ group in the polymethine chain linking the heterocyclic ring structures containing X and Y is substituted with a group selected from —CN, —Cl, —F, —$CF_3$ and —$C(O)R^{10}$ where $R^{10}$ is hereinbefore defined. Remaining $R^7$ groups that occur in the polymethine chain are hydrogen. A particularly preferred group $R^7$ in the dyes according to formula (1) is meso-substituted —CN, which confers an unexpected hypsochromic shift of approximately 40 nm in the emission spectrum, when compared with the corresponding unsubstituted analogue.

Preferably, X and Y are selected from bis-$C_1$–$C_4$ alkyl-substituted carbon, oxygen and sulphur. Particularly preferred groups X and Y are >$C(CH_3)_2$.

The target bonding group F, may be any group suitable for attaching the dye to a target material, such as a carrier material or a biological compound and as such will be well known to those skilled in the art. For example, the target bonding group may be a reactive group that can react under suitable conditions with a functional group of a target material. Alternatively, the target bonding group F may be a functional group and the target may contain the reactive constituent, such that the functional group of the dye may be reacted under suitable conditions with the reactive group of the target material. In either case, the target molecule becomes labelled with the dye according to formula (1). Preferred reactive groups may be selected from carboxyl, succinimidyl ester, sulpho-succinimidyl ester, isothiocyanate, maleimide, haloacetamide, acid halide, hydrazide, vinylsulphone, dichlorotriazine and phosphoramidite. Preferred functional groups may be selected from hydroxy, amino, sulphydryl, imidazole, carbonyl including aldehyde and ketone, phosphate and thiophosphate.

Suitably, $Z^1$ and $Z^2$ may be selected independently from the group consisting of phenyl, pyridinyl, naphthyl, indenyl, quinolinyl, indolyl, benzothiophenyl, benzofuranyl and benzimidazolyl moieties. Additional one ring or two fused ring systems will be readily apparent to the skilled person. Preferably, $Z^1$ and $Z^2$ are selected from the group consisting of phenyl, pyridinyl, naphthyl, quinolinyl and indolyl moieties. Particularly preferred $Z^1$ and $Z^2$ are phenyl and naphthyl moieties.

Preferably, the spacer group E is selected from:
—$(CHR')_p$—
—$\{(CHR')_q$—O—$(CHR')_r\}_s$—
—$\{(CHR')_q$—NR'—$(CHR')_r\}_s$—
—$\{(CHR')_q$—(CH=CH)—$(CHR')_r\}_s$—
—$\{(CHR')_q$—CO—NR'—$(CHR')_r\}_s$— where R' is hydrogen or $C_1$–$C_4$ alkyl; p is 1–20, preferably 1–10, q is 0–10, r is 1–10 and s is 1 or 2.

DETAILED DESCRIPTION OF THE PREFERRED EMBODIMENTS

Figure 1:
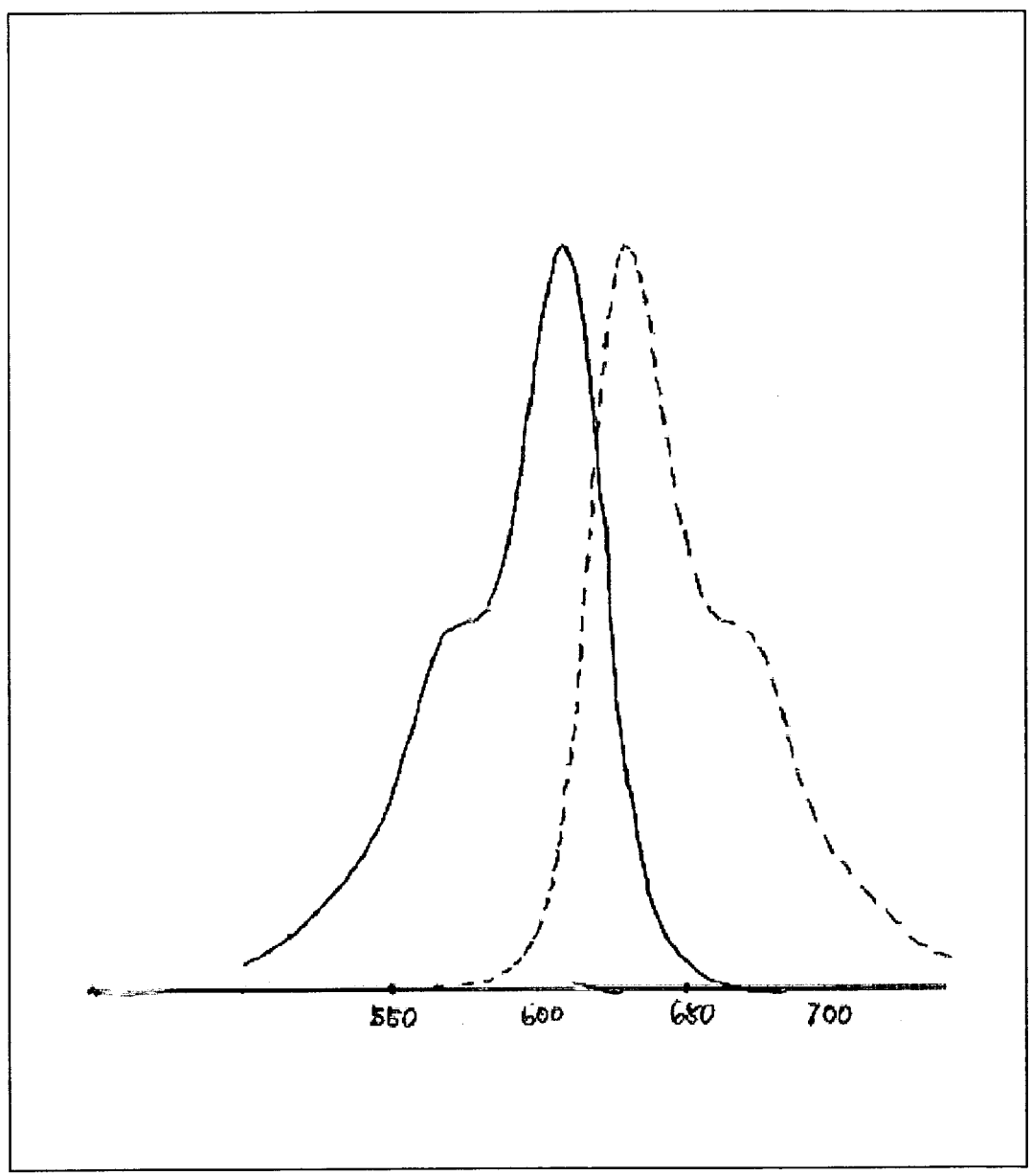
FIG. 1 shows the absorption and emission spectra of 2-{5-[1-(5-carboxypentyl)-3,3-dimethyl-1,3-dihydro-2H-indol-2-ylidene]-3-cyano-1,3-pentadienyl}-1,3,3-trimethyl-3H-indolinium (meso-cyano Cy5).

Specific examples of reactive groups $R^1$, $R^2$, $R^3$, $R^4$, $R^5$, $R^6$ (and $R^8$ and $R^9$ if present) in the dye according to formula (1) and the groups with which groups $R^1$, $R^2$, $R^3$, $R^4$, $R^5$, $R^6$ (and $R^8$ and $R^9$ if present) can react are provided in Table 3. In the alternative, $R^1$, $R^2$, $R^3$, $R^4$, $R^5$, $R^6$ (and $R^8$ and $R^9$ if present) may be the functional groups of Table 3 which would react with the reactive groups of a target molecule.

TABLE 3

Possible Reactive Substituents and Functional Groups Reactive Therewith

| Reactive Groups | Functional Groups |
| --- | --- |
| Succinimidyl esters | primary amino, secondary amino |
| Anhydrides, acid halides | primary amino, secondary amino, hydroxyl |
| Isothiocyanate | amino groups |
| Vinylsulphone | amino groups |
| Dichlorotriazines | amino groups |
| Haloacetamides, maleimides | thiols, imidazoles, hydroxyl, amines |
| Carboxyl | amino, hydroxyl, thiols |
| Phosphoramidites | hydroxyl groups |

Particularly suitable reactive groups $R^1$, $R^2$, $R^3$, $R^4$, $R^5$, $R^6$ (and $R^8$ and $R^9$ if present) which are especially useful for labelling target components with available amino and hydroxyl functional groups include:

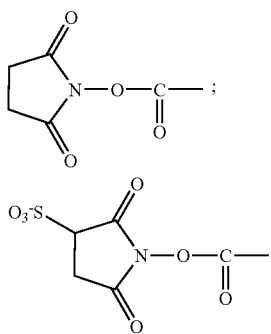

Particularly suitable reactive groups $R^1$, $R^2$, $R^3$, $R^4$, $R^5$, $R^6$ (and $R^8$ and $R^9$ if present) which are especially useful for labelling target components with available thiol functional groups include:

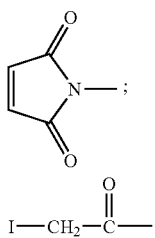

Aryl is an aromatic substituent containing one or two fused aromatic rings containing 6 to 10 carbon atoms, for example phenyl or naphthyl, the aryl being optionally and independently substituted by one or more substituents, for example halogen, straight or branched chain alkyl groups containing 1 to 10 carbon atoms, aralkyl and $C_1$–$C_6$ alkoxy, for example, methoxy, ethoxy, propoxy and n-butoxy.

Heteroaryl is a mono- or bicyclic 5 to 10 membered aromatic ring system containing at least one and no more than 3 heteroatoms which may be selected from N, O, and S and is optionally and independently substituted by one or more substituents, for example halogen, straight or branched chain alkyl groups containing 1 to 10 carbon atoms, aralkyl and $C_1$–$C_6$ alkoxy, for example, methoxy, ethoxy, propoxy and n-butoxy.

Aralkyl is a $C_1$–$C_6$ alkyl group substituted by an aryl or heteroaryl group.

Halogen and halo groups are selected from fluorine, chlorine, bromine and iodine.

Preferably, at least one of the groups $R^1$, $R^2$, $R^3$, $R^4$, $R^5$, $R^6$ (and $R^8$ and $R^9$ if present) in the dye of formula (1) comprises a water solubilising group for conferring a hydrophilic characteristic to the compound. Solubilising groups, for example, sulphonate, sulphonic acid and quaternary ammonium, may be attached directly to the aromatic ring structures $Z^1$ and/or $Z^2$. Alternatively, solubilising groups may be attached by means of a $C_1$ to $C_6$ alkyl linker chain to said aromatic ring structures and may be selected from the group —$(CH_2)_k$—W where W is selected from sulphonate, sulphonic acid, quaternary ammonium and carboxyl; and k is an integer from 1 to 6. Alternative solubilising groups may be carbohydrate residues, for example, monosaccharides. Examples of water solubilising constituents include $C_1$–$C_6$ alkyl sulphonates, such as —$(CH_2)_3$—$SO_3^-$ and —$(CH_2)_4$—$SO_3^-$. However, one or more sulphonate or sulphonic acid groups attached directly to the aromatic ring structures of a dye of formula (1) are particularly preferred. Water solubility may be advantageous when labelling biological target molecules, for example, proteins and nucleic acid derivatives.

An exemplary dye according to the first embodiment of the first aspect is 2-{5-[1-(5-carboxypentyl)-3,3-dimethyl-1,3-dihydro-2H-indol-2-ylidene]-3-cyano-1,3-pentadienyl}-1,3,3-trimethyl-3H-indolinium (meso-cyano Cy5).

The fluorescent dyes of the present invention may be used to covalently label and thereby impart fluorescent properties to a target material, and in particular, they may be used for labelling and detecting biological molecules. Thus, in a second aspect, there is provided a method for labelling a target material, the method comprising:

i) adding to a liquid containing said target material a fluorescent dye of formula (1):

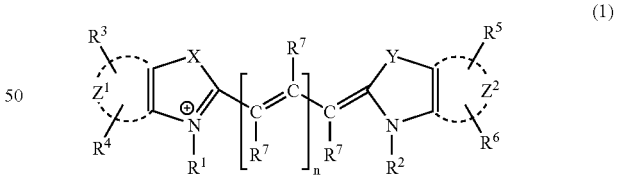

wherein:

groups $R^3$ and $R^4$ are attached to the $Z^1$ ring structure and groups $R^5$ and $R^6$ are attached to the $Z^2$ ring structure, and n=1, 2 or 3;

$Z^1$ and $Z^2$ independently represent the atoms necessary to complete one ring, or two fused ring aromatic or heteroaromatic systems, each ring having five or six atoms selected from carbon atoms and optionally no more than two atoms selected from oxygen, nitrogen and sulphur;

X and Y are the same or different and are selected from oxygen, sulphur, —CH=CH— and the group:

at least one of groups $R^1$, $R^2$, $R^3$, $R^4$, $R^5$, $R^6$ (and $R^8$ and $R^9$ if present) is the group -E-F where E is a spacer group having a chain from 1–20 atoms selected from the group consisting of carbon, nitrogen, oxygen, sulphur and phosphorus atoms and F is a target bonding group;

one of groups $R^7$ is selected from —CN, —Cl, —F, —CF$_3$ and —C(O)R$^{10}$ wherein R$^{10}$ is selected from H, $C_1$–$C_6$ alkyl and aryl;

remaining groups $R^7$ are hydrogen or two of $R^7$ together with the group:

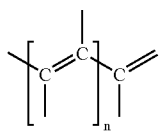

form a hydrocarbon ring system which may optionally contain a heteroatom selected from —O—, —S—, or >NH and n is hereinbefore defined;

when any of groups $R^3$, $R^4$, $R^5$ and $R^6$ is not said group -E-F, said remaining groups $R^3$, $R^4$, $R^5$ and $R^6$ are independently selected from hydrogen, halogen, hydroxyl, amino, mono- or di-$C_1$–$C_4$ alkyl-substituted amino, sulphydryl, carboxyl, $C_1$–$C_6$ alkoxy, $C_1$–$C_6$ alkyl, aryl, heteroaryl, aralkyl, sulphonate, sulphonic acid, quaternary ammonium and the group —(CH$_2$)$_k$—W;

when any of groups $R^8$ and $R^9$ is not said group -E-F, said remaining groups $R^8$ or $R^9$ are independently selected from $C_1$–$C_4$ alkyl and —(CH$_2$)$_k$—W;

when any of groups $R^1$ and $R^2$ is not said group -E-F, said remaining groups $R^1$ or $R^2$ are selected from hydrogen, $C_1$–$C_6$ alkyl, benzyl and —(CH$_2$)$_k$—W;

wherein W is selected from sulphonate, sulphonic acid, quaternary ammonium and carboxyl; and k is an integer from 1 to 6; and ii) incubating said fluorescent dye with said target material under conditions suitable for binding to and thereby labelling said target material.

The target bonding group F may be a reactive group for reacting with a functional group of the target material. Alternatively, the target bonding group may be a functional group for reacting with a reactive group on the target biological material. The method comprises incubating the target material with an amount of the dye according to the invention under conditions to form a covalent linkage between the target and the dye. The target may be incubated with an amount of a compound according to the present invention having at least one of groups $R^1$, $R^2$, $R^3$, $R^4$, $R^5$, $R^6$ (and $R^8$ and $R^9$ if present) that includes a reactive or functional group as hereinbefore defined that can covalently bind with the functional or reactive group of the target biological material.

Suitable target biological materials include, but are not limited to the group consisting of antibody, lipid, protein, peptide, carbohydrate, nucleotides which contain or are derivatized to contain one or more of an amino, sulphydryl, carbonyl, hydroxyl and carboxyl, phosphate and thiophosphate groups, and oxy or deoxy polynucleic acids which contain or are derivatized to contain one or more of an amino, sulphydryl, carbonyl, hydroxyl and carboxyl, phosphate and thiophosphate groups, microbial materials, drugs, hormones, cells, cell membranes and toxins.

Preferably, X and Y are selected from bis-$C_1$–$C_4$ alkyl-substituted carbon, oxygen and sulphur. Particularly preferred groups X and Y are >C(CH$_3$)$_2$.

Preferably, $R^7$ is meso-substituted —CN and remaining groups $R^7$ are hydrogen.

The fluorescent dyes according to the invention having a target bonding group F in at least one of groups $R^1$, $R^2$, $R^3$, $R^4$, $R^5$, $R^6$ (and $R^8$ and $R^9$ if present) may be used in an assay method for determining the presence, the amount, or the activity of an analyte in a sample. Thus, in a third aspect according to the present invention, there is provided a method for the assay of an analyte in a sample which method comprises:

i) contacting the analyte with a specific binding partner for said analyte under conditions suitable to cause the binding of at least a portion of said analyte to said specific binding partner to form a complex and wherein one of said analyte and said specific binding partner is labelled with a fluorescent dye of formula (1):

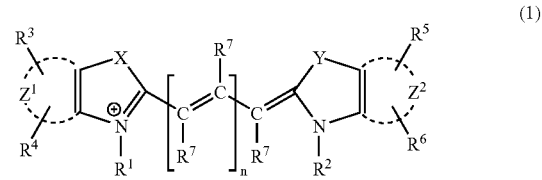

(1)

wherein:

groups $R^3$ and $R^4$ are attached to the $Z^1$ ring structure and groups $R^5$ and $R^6$ are attached to the $Z^2$ ring structure, and n=1, 2 or 3;

$Z^1$ and $Z^2$ independently represent the atoms necessary to complete one ring, or two fused ring aromatic or heteroaromatic systems, each ring having five or six atoms selected from carbon atoms and optionally no more than two atoms selected from oxygen, nitrogen and sulphur;

X and Y are the same or different and are selected from oxygen, sulphur, —CH═CH— and the group:

at least one of groups $R^1$, $R^2$, $R^3$, $R^4$, $R^5$, $R^6$ (and $R^1$ and $R^9$ if present) is the group -E-F where E is a spacer group having a chain from 1–20 atoms selected from the group consisting of carbon, nitrogen, oxygen, sulphur and phosphorus atoms and F is a target bonding group; one of groups $R^7$ is selected from —CN, —Cl, —F, —CF$_3$ and —C(O)R$^{10}$ wherein R$^{10}$ is selected from H, $C_1$–$C_6$ alkyl and aryl;

remaining groups $R^7$ are hydrogen or two of $R^7$ together with the group:

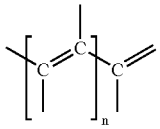

form a hydrocarbon ring system which may optionally contain a heteroatom selected from —O—, —S—, or >NH and n is hereinbefore defined;

when any of groups $R^3$, $R^4$, $R^5$ and $R^6$ is not said group -E-F, said remaining groups $R^3$, $R^4$, $R^5$ and $R^6$ are independently selected from hydrogen, halogen, hydroxyl, amino, mono- or di-$C_1$–$C_4$ alkyl-substituted amino, sulphydryl, carboxyl, $C_1$–$C_6$ alkoxy, $C_1$–$C_6$ alkyl, aryl, heteroaryl, aralkyl, sulphonate, sulphonic acid, quaternary ammonium and the group —$(CH_2)_k$—W;

when any of groups $R^8$ and $R^9$ is not said group -E-F, said remaining groups $R^8$ or $R^9$ are independently selected from $C_1$–$C_4$ alkyl and —$(CH_2)_k$—W;

when any of groups $R^1$ and $R^2$ is not said group -E-F, said remaining groups $R^1$ or $R^2$ are selected from hydrogen, $C_1$–$C_6$ alkyl, benzyl and —$(CH_2)_k$—W;

wherein W is selected from sulphonate, sulphonic acid, quaternary ammonium and carboxyl; and k is an integer from 1 to 6;

ii) measuring the emitted fluorescence of the labelled complex; and iii) correlating the emitted fluorescence with the presence or the amount of said analyte in said sample.

In one embodiment, the assay method is a direct assay for the measurement of an analyte in a sample. Optionally, a known or putative inhibitor compound may be included in the assay mix, in which case, the measurement may be correlated with the biological activity of the known or putative inhibitor.

In a second, or alternative embodiment, the assay may be a competitive assay wherein a sample containing an analyte competes with a fluorescent tracer for a limited number of binding sites on a binding partner that is capable of specifically binding the analyte and the tracer. Suitably, the tracer is a labelled analyte or a labelled analyte analogue, in which the label is a fluorescent dye of formula (1). Increasing amounts (or concentrations) of the analyte in the sample will reduce the amount of the fluorescent labelled analyte or fluorescent labelled analyte analogue that is bound to the specific binding partner. The fluorescence signal is measured and the concentration of analyte may be obtained by interpolation from a standard curve.

In a further embodiment, the binding assay may employ a two-step format, wherein a first component, which may be optionally coupled to an insoluble support, is bound to a second component to form a specific binding complex, which is bound in turn to a third component. In this format, the third component is capable of specifically binding to either the second component, or to the specific binding complex. Either of the second or the third component may be labelled with a fluorescent dye according to the present invention. Examples include "sandwich" assays, in which one component of a specific binding pair, such as a first antibody, is coated onto a surface, such as the wells of a multiwell plate. Following the binding of an antigen to the first antibody, a fluorescent labelled second antibody is added to the assay mix, so as to bind with the antigen-first antibody complex. The fluorescence signal is measured and the concentration of antigen may be obtained by interpolation from a standard curve.

Examples of analyte-specific binding partner pairs include, but are not restricted to, antibodies/antigens, lectins/glycoproteins, biotin/streptavidin, hormone/receptor, enzyme/substrate or co-factor, DNA/DNA, DNA/RNA and DNA/binding protein. It is to be understood that any molecules which possess a specific binding affinity for each other may be employed, so that the fluorescent dyes of the present invention may be used for labelling one component of a specific binding pair, which in turn may be used in the detection of binding to the other component.

The fluorescent dyes according to first embodiment of the first aspect may be used in applications that include detecting and distinguishing between various components in a mixture. Thus, in a fourth aspect, the present invention provides a set of two or more different fluorescent dyes wherein at least one dye of said set is a fluorescent dye of formula (1):

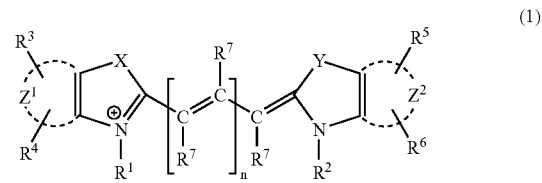

wherein:

groups $R^3$ and $R^4$ are attached to the $Z^1$ ring structure and groups $R^5$ and $R^6$ are attached to the $Z^2$ ring structure, and n=1, 2 or 3;

$Z^1$ and $Z^2$ independently represent the atoms necessary to complete one ring, or two fused ring aromatic or heteroaromatic systems, each ring having five or six atoms selected from carbon atoms and optionally no more than two atoms selected from oxygen, nitrogen and sulphur;

X and Y are the same or different and are selected from oxygen, sulphur, —CH=CH— and the group:

at least one of groups $R^1$, $R^2$, $R^3$, $R^4$, $R^5$, $R^6$ (and $R^8$ and $R^9$ if present) is the group -E-F where E is a spacer group having a chain from 1–20 atoms selected from the group consisting of carbon, nitrogen, oxygen, sulphur and phosphorus atoms and F is a target bonding group;

one of groups $R^7$ is selected from —CN, —Cl, —F, —$CF_3$ and —$C(O)R^{10}$ wherein $R^{10}$ is selected from H, $C_1$–$C_6$ alkyl and aryl; remaining groups $R^7$ are hydrogen or two of $R^7$ together with the group:

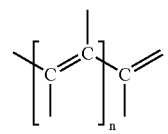

form a hydrocarbon ring system which may optionally contain a heteroatom selected from —O—, —S—, or>NH and n is hereinbefore defined;

when any of groups $R^3$, $R^4$, $R^5$ and $R^6$ is not said group -E-F, said remaining groups $R^3$, $R^4$, $R^5$ and $R^6$ are independently selected from hydrogen, halogen, hydroxyl, amino, mono- or di-$C_1$–$C_4$ alkyl-substituted amino, sulphydryl, carboxyl, $C_1$–$C_6$ alkoxy, $C_1$–$C_6$ alkyl, aryl, heteroaryl, aralkyl, sulphonate, sulphonic acid, quaternary ammonium and the group —$(CH_2)_k$—W;

when any of groups $R^8$ and $R^9$ is not said group -E-F, said remaining groups $R^8$ or $R^9$ are independently selected from $C_1$–$C_4$ alkyl and —$(CH_2)_k$—W;

when any of groups $R^1$ and $R^2$ is not said group -E-F, said remaining groups $R^1$ or $R^2$ are selected from hydrogen, $C_1$–$C_6$ alkyl, benzyl and —$(CH_2)_k$—W;

wherein W is selected from sulphonate, sulphonic acid, quaternary ammonium and carboxyl; and k is an integer from 1 to 6; and wherein each dye of said set has a distinguishably different fluorescence emission wavelength compared with the emission wavelengths of the remaining dyes of the set.

Preferably, the set of fluorescent dyes according to the fourth aspect will comprise four different dyes, each dye of the set having a different fluorescence emission wavelength.

Preferably, X and Y are selected from bis-$C_1$–$C_4$ alkyl-substituted carbon, oxygen and sulphur. Particularly preferred groups X and Y are >$C(CH_3)_2$.

Preferably, $R^7$ is meso-substituted —CN and remaining groups $R^7$ are hydrogen.

The set of dyes may be used in a detection method wherein different fluorescent dyes of the set of dyes are covalently bonded to a plurality of different primary components, each primary component being specific for a different secondary component, in order to identify each of a plurality of secondary components in a mixture of secondary components. The method comprises covalently binding different dyes of a set of fluorescent dyes according to the fourth aspect of the invention to different primary components in a multicomponent mixture wherein each dye of the set has a different fluorescence wavelength, compared with the fluorescence wavelength of the remaining dyes of the set; adding the dye-labelled primary components to a preparation containing secondary components under conditions to enable binding of at least a portion of each of said dye-labelled primary components to its respective secondary component; and determining the presence or the amount of the bound secondary component by measuring the fluorescence intensity of each of the labelled primary component-secondary component complexes at their respective fluorescence wavelengths.

If required, any unreacted primary components may be removed or separated from the preparation by, for example washing, to prevent interference with the analysis.

The set of fluorescent dyes according to the present invention may be used in any system in which the creation of a fluorescent primary component is possible. For example, an appropriately reactive fluorescent dye according to the invention can be conjugated to a DNA or RNA fragment and the resultant conjugate then caused to bind to a complementary target strand of DNA or RNA. Other examples of primary component-secondary component complexes which may be detected include antibodies/antigens and biotin/streptavidin.

The set of dyes according to the present invention may also be advantageously used in fluorescent DNA sequencing based upon fluorescence wavelength discrimination of the DNA fragments. Briefly, each one of a set of dyes, may be coupled to a primer. Various primers are available, such as primers from pUC/M13, λgt10, λgt11 and the like (see Sambrook et al, Molecular Cloning, A Laboratory Manual 2$^{nd}$ Edition, Cold Spring Harbour Laboratory Press 1989). DNA sequences are cloned into an appropriate vector having a primer sequence joined to the DNA fragment to be sequenced. After hybridisation to the DNA template, polymerase enzyme-directed synthesis of a complementary strand occurs. Different 2',3'-dideoxynucleotide terminators are employed in each different sequencing reaction so as to obtain base-specific termination of the chain extension reaction. The resulting set of DNA fragments are separated by electrophoresis and the terminating nucleotide (and thus the DNA sequence) is determined by detecting the fluorescence emission of the labelled fragments. DNA sequencing may also be performed using dideoxynucleotide terminators covalently labelled with the fluorescent dyes according to the present invention.

The non-fluorescent or substantially non-fluorescent dyes according to the second embodiment of the first aspect may be used as one component of a fluorescent donor/acceptor pair for assays involving the detection of binding and/or cleavage events in reactions involving biological molecules by means of fluorescence resonance energy transfer (FRET). Such methods are described in European Patent Application No. 1086179 A1.

Thus, in a fifth aspect, the invention relates to an assay method comprising:

i) separating two components which are in an energy transfer relationship, the first component being labelled with a fluorescent donor dye and the second component being labelled with a non-fluorescent or substantially non-fluorescent acceptor dye according to formula (1) wherein groups $R^1$, $R^2$, $R^3$, $R^4$, $R^5$, $R^6$, $R^7$, $Z^1$, $Z^2$, X and Y are hereinbefore defined and wherein at least one of groups $R^1$, $R^2$, $R^3$, $R^4$, $R^5$ and $R^6$ comprises at least one nitro group; and ii) detecting the presence of the first component by measuring emitted fluorescence.

In a sixth aspect the invention relates to an assay method comprising:

i) binding one component of a specific binding pair with a second component of said pair, said first component being labelled with a fluorescent donor dye and said second component being labelled with a non-fluorescent or substantially non-fluorescent acceptor dye according to formula (1) wherein groups $R^1$, $R^2$, $R^3$, $R^4$, $R^5$, $R^6$, $R^7$, $Z^1$, $Z^2$, X and Y are hereinbefore defined and wherein at least one of groups $R^1$, $R^2$, $R^3$, $R^4$, $R^5$ and $R^6$ comprises at least one nitro group; so as to bring about an energy transfer relationship between said first and second components; and, ii) detecting the binding of the first and second components by measuring emitted fluorescence.

According to the method, when a non-fluorescent, or substantially non-fluorescent acceptor dye is in an energy transfer relationship with a fluorescent donor dye, the fluorescence emission of the donor is reduced through quenching by the acceptor. When resonance energy transfer is lost through separation of the fluorescent donor dye and the acceptor dye, the fluorescence emission due to the donor dye is restored. Effective non-fluorescent quenching dyes have a low efficiency for converting absorbed incident light into fluorescence and, as such, are unsuitable as fluorescent labels. The intrinsic fluorescence of the non-fluorescent or substantially non-fluorescent cyanine dyes according to the present invention, when they are employed as energy acceptors, is preferably less than 15%, more preferably less than 10%, of the fluorescence emission of the donor dye upon excitation at the donor excitation wavelength and detection of emission at the donor emission wavelength. Moreover, the dyes are designed such that their spectral overlap with a fluorescent cyanine donor dye is maximised, thereby improving efficiency of quenching.

The biological material can be a biological molecule which may be cleaved into the two component parts; or the biological material may comprise two components as hereinbefore defined, which may be bound either by covalent or non-covalent association.

Suitable fluorescent donor dyes that can be combined with the non-fluorescent cyanine acceptor dyes to form energy transfer pairs in assay methods according to the fifth and sixth aspects include the well known reactive analogues of the fluorescein, rhodamine and cyanine dyes. Other low molecular weight fluorescent dyes may be selected from the derivatives of the bis-pyrromethine boron difluoride dyes, such as 3,3',5,5'-tetramethyl-2,2'-pyrromethine-1,1'-boron difluoride, sold under the trademark BODIPY by Molecular Probes Inc. Particularly preferred are the cyanine dyes.

Suitable fluorescein donor dyes include: 5- and 6-carboxyfluorescein and 6-carboxy-4',5'-dichloro-2',7'-dimethoxyfluorescein. Suitable rhodamine dyes include: 5- and 6-carboxyrhodamine (Rhodamine 110), 5-carboxyrhodamine-6G (R6G-5 or REG-5), 6-carboxyrhodamine-6G (R6G-6 or REG-6), N,N,N',N'-tetramethyl-5- and 6-carboxyrhodamine (TAMRA or TMR), 5- and 6-carboxy-X-rhodamine (ROX).

Suitable cyanine donor dyes include the CyDyeS™: Cy3, Cy3.5, Cy5 and Cy5.5. Cyanine dyes suitable for use as the donor component in the assay of the present invention are disclosed in U.S. Pat. No. 5,268,486 and U.S. Pat. No. 6,048,982 (Waggoner, A. S.), or the rigidised trimethine cyanine dyes such as those disclosed in U.S. Pat. No. 6,133,445 (Waggoner et al).

The assays may be performed according to the present invention in high throughput screening applications, including those in which compounds are to be screened for their inhibitory effects, potentiation effects, agonistic, or antagonistic effects on the reaction under investigation. Examples of such assays include, but are not restricted to, the cleavage of a peptide or protein by a protease and the cleavage of a DNA or RNA molecule by a nuclease. In this assay format, the enzyme substrate (peptide or nucleic acid) will include a sequence whose structure combines a fluorescent donor dye molecule with the non-fluorescent cyanine acceptor dye, attached to the substrate at either side of the substrate bond to be cleaved. The substrate joins the fluorescent donor and the acceptor moieties in close proximity. The intrinsic fluorescence of the donor is reduced through quenching by the acceptor due to resonance energy transfer between the pair of dyes. Resonance energy transfer becomes insignificant when the distance between the donor and acceptor moieties is greater than about 100 Angstroms. Cleavage of the substrate results in the separation between donor and acceptor dyes and concomitant loss of resonance energy transfer. The fluorescence signal of the donor fluorescent dye increases, thereby enabling accurate measurement of the cleavage reaction.

Briefly, an assay for the detection of proteolytic enzyme activity may be configured as follows. A reaction mixture is prepared by combining a protease enzyme and a fluorogenic substrate which combines a fluorescent donor dye molecule with a non-fluorescent acceptor dye of formula (1) attached to the substrate at either side of the substrate bond to be cleaved. A known or a putative protease inhibitor compound may be optionally included in the reaction mixture. Typically the reaction is performed in buffered solution and the reaction is allowed to proceed to completion. The progress of the reaction may be monitored by observing the steady state fluorescence emission due to the fluorescent donor dye, which is recorded using a spectrofluorimeter.

Alternatively, the invention relates to an assay method for detecting and measuring binding, by covalent or non-covalent association, of one component of a ligand/reactant pair with a second component of said pair, said first component being labelled with a fluorescent donor dye and said second component being labelled with a non-fluorescent cyanine acceptor dye according to the invention. Such assays are conveniently categorised as one of two types.

I. The first category comprises equilibrium binding assays, in which one component of a specific binding pair binds non-covalently to a second component of the specific binding pair. Such equilibrium binding assays may be applied to screening assays in which samples containing compounds to be screened are tested for their effect upon the binding of the first component of the specific binding pair (either antagonistic or agonistic), to the second component. Either component may be labelled with the donor dye or the acceptor dye. In the absence of binding, the labelled components are too far apart for resonance energy transfer to occur. Upon binding of one labelled component to its labelled specific binding partner, the label moieties are brought into sufficiently close proximity for energy transfer to occur between donor and acceptor species resulting in a quenching of the donor fluorescence and a decrease in donor fluorescent signal.

For example, the dyes used in the present invention can be used to label probes such as those described by Tyagi and Kramer (Nature Biotechnology, (1996), 14, 303–8) for use in the detection and identification of unique DNA sequences or specific genes in a complete DNA molecule or mixtures of nucleic acid fragments. One end of the nucleic acid probe is labelled with a fluorescent dye and at the other end with a non-fluorescent cyanine acceptor dye according to the present invention. In the absence of specific target sequence, the fluorescent and quenching species will be held sufficiently close for energy transfer to occur. Consequently, irradiation of the fluorophore by excitation light will give reduced fluorescent signal. Interaction of the probe with a specific target nucleic acid sequence causes a conformational change to take place in the probe, such that the fluorescent donor and acceptor become separated by distance. Excitation of the fluorophore will result in a fluorescent signal which may be recorded using a spectrofluorimeter.

Alternatively, the equilibrium binding assay may employ a sandwich assay format in which one component of a specific binding pair, such as a first antibody, is coated onto the wells of a microtitre well plate. Following binding of an antigen to the first antibody, a second antigen-specific antibody is then added to the assay mix, so as to bind with the antigen-first antibody complex. In this format, either the first antibody or the antigen may be labelled with the donor dye and the second antibody labelled with the acceptor dye or vice versa. In the absence of binding of the first antibody-antigen-second antibody complex, the labelled components are too far apart for resonance energy transfer to occur. Upon binding of the second antibody with the first antibody-antigen complex, the label moieties are brought into sufficiently close proximity for energy transfer to occur between donor and acceptor species resulting in a quenching of the donor fluorescence and a decrease in donor fluorescent signal. Fluorescence signal is measured and the concentration of antigen may be determined by interpolation from a standard curve. Examples of specific binding pairs are as described hereinbefore.

II. In the second category, the assay may comprise detection and measurement of the addition of a fluorescent donor dye labelled moiety (the reactant) in solution in the assay medium to a non-fluorescent acceptor dye-labelled moiety (the substrate) or vice versa, by covalent attachment mediated through enzyme activity. Examples of such assays include, but are not restricted to, the joining of DNA or RNA molecules to other nucleic acid molecules by ligases, the addition of a nucleotide to a DNA or RNA molecule by a polymerase and the transfer of a labelled chemical moiety from one molecule to another by a transferase such as acetyl transferase. A known or a putative enzyme inhibitor may be optionally included in the reaction mixture. It is to be understood that any two appropriate reactant and substrate moieties may be employed. Either of the donor or the acceptor dyes of the present invention may be used for labelling one moiety which in turn may be used in the detection and measurement of the reaction with the substrate.

For example, in a DNA ligation assay, DNA molecules to be joined are mixed together in aqueous buffer containing ATP in the presence of a DNA ligase. Following incubation, the DNA strands are covalently attached in the correct configuration by the formation of standard phosphodiester linkages in both strands of the duplex. Upon joining the label moieties are bought into sufficiently close proximity for energy transfer to occur between donor and acceptor species resulting in a quenching of the donor fluorescence and a signal decrease which is proportional to the amount of ligated product formed.

The invention also relates to labelling methods wherein the dyes according to formula (1) including at least one reactive or functional group at the $R^1$ to $R^6$ positions covalently react with amino, hydroxyl, aldehyde, phosphoryl, carboxyl, sulphydryl or other reactive groups on target materials. Such target materials include, but are not limited to the group consisting of antigen, antibody, lipid, protein, peptide, carbohydrate, nucleotides which contain or are derivatized to contain one or more of an amino, sulphydryl, carbonyl, hydroxyl and carboxyl, phosphate and thiophosphate groups, and oxy or deoxy polynucleic acids which contain or are derivatized to contain one or more of an amino, sulphydryl, carbonyl, hydroxyl and carboxyl, phosphate and thiophosphate groups, microbial materials, drugs and toxins.

The dyes of formula (1) may be prepared by a process comprising:

a) reacting a first compound having the formula (A):

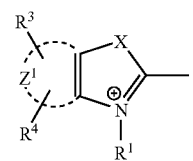

(A)

where X, $Z^1$, $R^1$, $R^3$ and $R^4$ are hereinbefore defined;

b) a second compound which is the same or different from the first compound and having the formula (B):

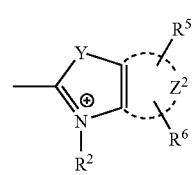

(B)

where Y, $Z^2$, $R^2$, $R^5$, $R^6$ are hereinbefore defined, and c) a third compound (C) suitable for forming a linkage between the first and second compounds, wherein (A), (C) and (B) are reacted either in a single step or a multiple step process to form the compounds of formula (1).

Symmetrical compounds of formula (1) wherein structures (A) and (B) are the same may be suitably prepared by reacting a compound of formula (A) (or (B)) in two molar proportions with an appropriate bis-functional methine fragment containing 1, 3 or 5 carbon atoms, wherein the central or meso carbon atom is appropriately substituted. For example, a substituted N,N'-diphenylformamidine, or ortho ester will be employed as the third compound (C) for preparing Cy3 and derivatives. In a corresponding manner, a suitably substituted malondialdehyde dianil may be employed for preparing the Cy5 analogues and a glutaconic aldehyde for preparing Cy7 analogues. The reaction is usually carried out in an organic solvent, such as pyridine and heated to reflux. The mixture subsequently is cooled and poured into an organic solvent such as ether. The resulting solid or semi-solid may be purified by chromatography on a silica gel column using a series of methanol/chloroform solvents.

Unsymmetrical compounds of formula (1) wherein structures (A) and (B) are different may be conveniently prepared in a two step process. In this process, an intermediate dye compound is first formed by reacting an indolenine compound of formula (A) with a compound suitable for forming the linkage, for example, a suitably substituted N,N'-diphenylformamidine, or malonaldehyde dianil, in the presence of acetic anhydride, to form a 2-anilinovinyl or 4-anilino-1,3-butadienyl quaternary salt. The intermediate quaternary salt may be reacted with a second 2-methyl indolenine quaternary salt to give a compound of formula (1). Alternative intermediates for forming the polymethine linkage joining the heterocyclic ring systems are known and are described for example in Hamer, F. M., "The Cyanine Dyes and Related Compounds", Interscience (1964). Reagents suitable for forming the linkage in preferred compounds according to the invention, wherein the meso position is substituted with a cyano group, include cyanoacetic acid.

It will be readily appreciated that certain dyes of the present invention may be useful as intermediates for conversion to other dyes by methods well known to those skilled in the art. The dyes of the present invention may be synthesized by the methods disclosed herein. Derivatives of the compounds having a particular utility are prepared either by selecting appropriate precursors or by modifying the resultant compounds by known methods to include functional groups at a variety of positions. As examples, the dyes of the present invention may be modified to include certain reactive groups for preparing a dye according to the present invention, or charged or polar groups may be added to enhance the solubility of the compound in polar or nonpolar solvents or materials. As examples of conversions, an ester may be converted to a carboxylic acid or may be converted to an amido derivative. Groups $R^1$, $R^2$, $R^3$, $R^4$, $R^5$, $R^6$, $Z^1$, $Z^2$, X and Y may be chosen so that the dyes of the present invention have different wavelength characteristics, thereby providing a number of related dyes which can be used in multiparameter analyses wherein the presence and quantity of different compounds in a single sample may be differentiated based on the wavelengths of a number of detected fluorescence emissions. The dyes of the present invention may be made soluble in aqueous, other polar, or non-polar media containing the material to be labelled by appropriate selection of R-groups.

Cy™ is a trademark of Amersham Biosciences UK Limited.

EXAMPLES

The following example are illustrative of certain preferred embodiments of the instant invention but are not intended to be illustrative of all embodiments.

1. Preparation of 2-{[3,3-Dimethyl-1,3-dihydro-2H-indol-2-ylidene]-3-cyano-1,3-pentadienyl}-1,3,3-trimethyl-3H-indolinium

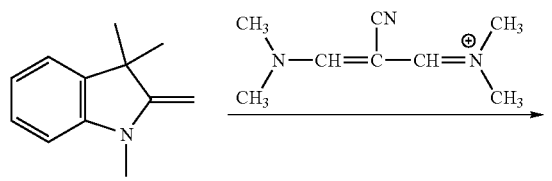

1.1 N-[2-Cyano-3-(dimethylamino)-2-propenylidene]-N-methylmethanaminium

To 25 mmoles of cyanoacetic acid in 15 ml of dry dimethylformamide was added 50 mmoles of chloromethylene dimethylammonium chloride (Aldrich, Catalogue #28,090-9). Immediately, the solution turned yellow and an exothermic reaction was observed. The reactants were allowed to stand at room temperatures overnight. The product was evaporated to dryness and used in the next step without further purification.

1.2 2-{5-[1,3,3-Trimethyl-1,3-dihydro-2H-indol-2-ylidene]-3-cyano-1,3-pentadienyl}-1,3,3-trimethyl-3H-indolinium To 50 mmoles of the Fisher base (2-methylene-1,3,3-trimethylindolenine; Aldrich Catalogue # M4620-9) in acetic anhydride (40 ml) and slight excess of sodium acetate (2.2 g), was added the product from the previous step (Section 1.1) dissolved in acetic anhydride (10 ml). The reaction was allowed to proceed at room temperature for four hours. The desired cyano-trimethine cyanine was isolated following silica gel column chromatography (X2) and elution with 30% MeOH in ethyl acetate.

2. Preparation of 2-{5-[1-(5-Carboxypentyl)-3,3-dimethyl-1,3-dihydro-2H-indol-2-ylidene]-3-cyano-1,3-pentadienyl}-1,3,3-trimethyl-3H-indolinium (meso-cyano Cy5)

2.1 2-{N-Acetyl-N-phenl}aminoethenyl-1,3,3-trimethylindolenine

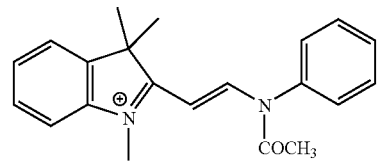

1,2,3,3-Tetramethyl-3H-indolium iodide (5 mmoles) and N,N'-diphenylforamidine (5 mmoles) in acetic anhydride (20 ml) was refluxed, under argon for four hours. After standing overnight, at room temperature, a crystalline precipitate was obtained. The precipitate was filtered, washed with ether and dried. NMR analysis indicated that it was the desired product.

2.2 2-{N-Acetyl-N-phenyl}aminoethenyl-1-{6-carboxypentyl}-3,3-trimethylindolenine

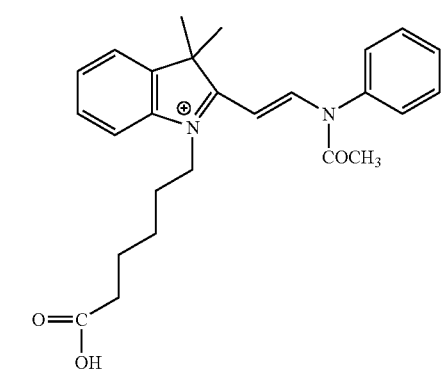

2,3,3-Trimethylindolenine (1 equivalent) was reacted with 6-bromohexanoic acid (2 equivalents) in 1,2-dichlorobenzene at 100° C. for 24 hours. The product was purified by flash chromatography on silica gel and the desired portion evaporated down to dryness to give 1-(6-carboxypentyl)-2,3,3-trimethylindolenine.

1-(6-Carboxypentyl)-2,3,3-trimethylindolenine was reacted with diphenylformamidine according to the method described in section 2.1 to give 2-{N-acetyl-N-phenyl}aminoethenyl-1-{6-carboxypentyl}-3,3-trimethylindolenine.

2.3 2-{5-[1-(5-Carboxypentyl)-3,3-dimethyl-1,3-dihydro-2H-indol-2-ylidene]-3-cyano-1,3-pentadienyl}-1,3,3-trimethyl-3H-indolinium (meso-cyano Cy5)

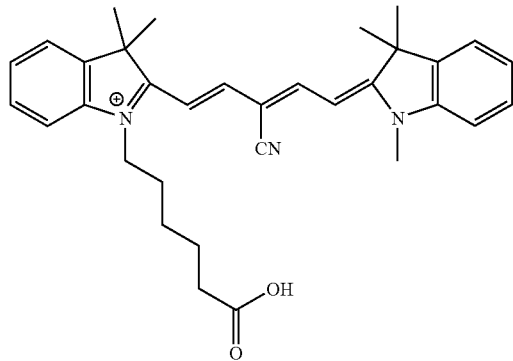

2-{N-Acetyl-N-phenyl}aminoethenyl-1,3,3-trimethylindoleriine and 2-{N-acetyl-N-phenyl}aminoethenyl-1-{6-carboxypentyl}-3,3-trimethylindolenine (20 mmoles of each) and 10 equivalents of cyanoacetic acid in pyridine (100 ml) were heated under reflux under Argon for 4 hours. At the end of the reaction, the pyridine was evaporated and the product purified by repeated HPLC purification followed by silica gel column chromatography with increasing amounts of MeOH in ethyl acetate as the eluant to give a pure product, 2-{5-[1-(5-carboxypentyl)-3,3-dimethyl-1,3-dihydro-2H-indol-2-ylidene]-3-cyano-1,3-pentadienyl}-1,3,3-trimethyl-3H-indolinium (meso-cyano Cy5). Absorption maximum (MeOH): 610 nm: Emission maximum (MeOH): 628 nm; Quantum yield: 0.65 that of Cy5.

The product was found to be more stable than Cy5 according to the following criteria:
a) Photostability: (an ethanolic solution left in the room light). Half-life ($t_{1/2}$) for fading of the dyes: meso-cyano Cy5, $t_{1/2}$>>75 hours (Cy5,=22 hours);
b) Hydrolytic stability: (in de-ionized water with pH=6.85) Half-life ($t_{1/2}$) for fading of the dyes: meso-cyano Cy5, $t_{1/2}$>>150 hours (Cy5, $t_{1/2}$=56 hours).

Figure 2:
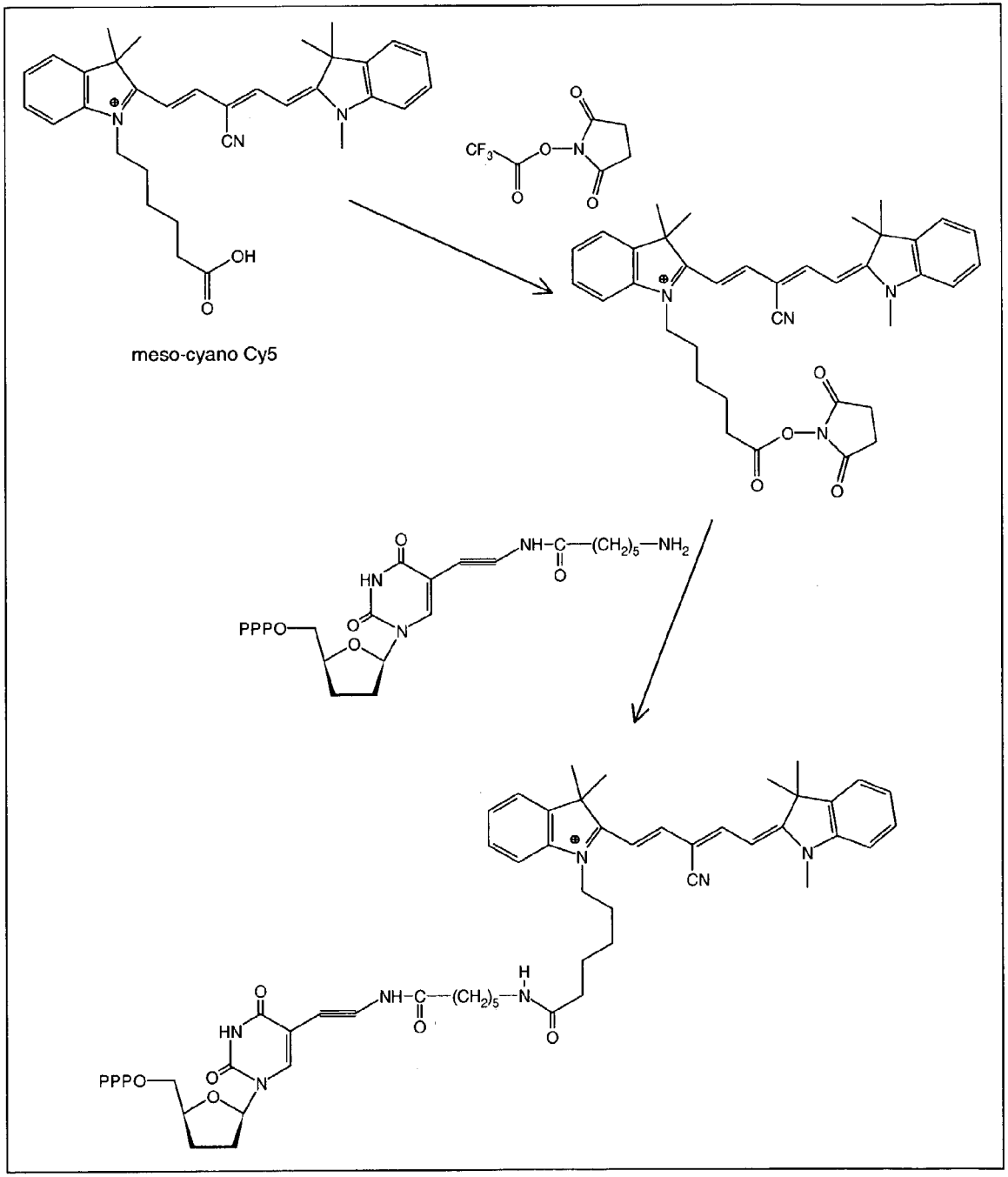
FIG. 2 is a reaction scheme illustrating the conjugation of 2-{5-[1-(5-carboxypentyl)-3,3-dimethyl-1,3-dihydro-2H-indol-2-ylidene]-3-cyano-1,3-pentadienyl}1,3,3-trimethyl-3H-indolinium with dideoxyuridine-5'-triphosphate.

3. Conjugation of 2-{5-[1-(5-carboxypentyl)-3,3-dimethyl-1,3-dihydro-2H-indol-2-ylidene]-3-cyano-1,3-pentadienyl}-1,3,3-trimethyl-3H-indolinium with dideoxyuridine-5'-triphosphate (FIG. 2)

3.1 Preparation of 2-{5-[1-(5-carboxypentyl)-3,3-dimethyl-1,3-dihydro-2H-indol-2-ylidene]-3-cyano-1,3-pentadienyl}-1,3,3-trimethyl-3H-indolinium, N-hydroxysuccinimidyl ester 2-{5-[1-(5-Carboxypentyl)-3,3-dimethyl-1,3-dihydro-2H-indol-2-ylidene]-3-cyano-1,3-pentadienyl}-1,3,3-trimethyl-3H-indolinium (20 mg; 45 micromoles) was dissolved in 20 ml of dichloromethane. To the solution was added 7 µl of pyridine, followed by 19 mg of trifluoroacetic acid succinimidyl ester (TFA-NHS) and stirred under argon at room temperature for 30 minutes. At such time, a quantitative conversion was observed as shown by the thin layer chromatography (TLC) of the crude product. The reaction was diluted to 10 ml with dichloromethane and extracted with 3×10 ml portions of water. The organic phase was evaporated to dryness and co-evaporated three times with acetonitrile. The product thus obtained, weighed 24 mg.

3.2 Conjugation of 2-{5-[1-(5-carboxypentyl)-3,3-dimethyl-13-dihydro-2H-indol-2-ylidene]-3-cyano-1,3-pentadienyl}-1,3,3-trimethyl-3H-indolinium, N-hydroxysuccinimidyl ester with 11-dideoxyUTP 2-{5-[1-(5-Carboxypentyl)-3,3-dimethyl-1,3-dihydro-2H-indol-2-ylidene]-3-cyano-1,3-pentadienyl}-1,3,3-trimethyl-3H-indolinium,-N-hydroxysuccinimidyl ester (2 mg, ca. 2.8 micromoles), obtained as in 2.1), was dissolved in 200 µl of dimethyl formamide (DMF) and mixed with 2 micromoles of 11-ddUTP in 200 µl of 0.1 M $NaHCO_3$ with pH at 8.5. The mixture was left at ambient temperature overnight. The progress of the reaction was monitored by HPLC and the desired product purified through a C18 column to give 0.46 micromoles of the 2-{5-[1-(5-carboxypentyl)-3,3-dimethyl-1,3-dihydro-2H-indol-2-ylidene]-3-cyano-1,3-pentadienyl}-1,3,3-trimethyl-3H-indolinium-11ddUTP conjugate.

It is apparent that many modifications and variations of the invention as hereinabove set forth may be made without departing from the spirit and scope thereof. The specific embodiments described are given by way of example only, and the invention is limited only by the terms of the appended claims.

What is claimed is:
1. A dye of formula (1):

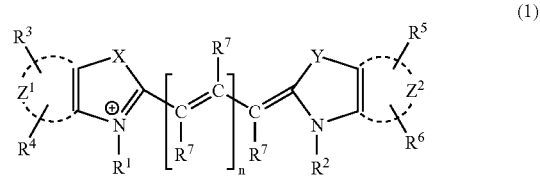

wherein:
groups $R^3$ and $R^4$ are attached to the $Z^1$ ring structure and groups $R^5$ and $R^6$ are attached to the $Z^2$ ring structure, and n=1, 2 or 3;
$Z^1$ and $Z^2$ independently represent the atoms necessary to complete one ring, or two fused ring aromatic or heteroaromatic systems, each ring having five or six atoms selected from carbon atoms and optionally no more than two atoms selected from oxygen, nitrogen and sulphur;
X and Y are the same or different and are selected from oxygen, sulphur, —CH═CH— and the group:

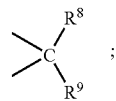

at least one of groups $R^1$, $R^2$, $R^3$, $R^4$, $R^5$, $R^6$ (and $R^8$ and $R^9$ if present) is the group -E-F where E is a spacer group having a chain from 1–20 atoms selected from the group consisting of carbon, nitrogen, oxygen, sulphur and phosphorus atoms and F is a reactive group selected from succinimidyl ester, sulpho-succinimidyl ester, isothiocyanate, maleimide, haloacetamide, acid halide, hydrazide, vinylsulphone, dichlorotrazine and phosphoramidite;

one of groups $R^7$ is selected from —CN and —$CF_3$;

remaining groups $R^7$ are hydrogen or two of $R^7$ together with the group:

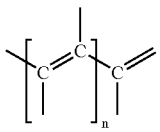

form a hydrocarbon ring system which may optionally contain a heteroatom selected from —O—, —S—, or >NH and n is hereinbefore defined;

when any of groups $R^3$, $R^4$, $R^5$ and $R^6$ is not said group -E-F, said remaining groups $R^3$, $R^4$, $R^5$ and $R^6$ are independently selected from hydrogen, halogen, hydroxyl, amino, mono- or di-$C_1$-$C_4$ alkyl-substituted amino, sulphydryl, nitro, mono- or di-nitro substituted benzyl, carboxyl, $C_1$-$C_6$ alkoxy, $C_1$-$C_6$ alkyl, aryl, heteroaryl, aralkyl, sulphonate, sulphonic acid, quaternary ammonium and the group —$(CH_2)_k$—W;

when any of groups $R^8$ and $R^9$ is not said group -E-F, said remaining groups $R^8$ or $R^9$ are independently selected from $C_1$-$C_4$ alkyl and —$(CH_2)_k$—W;

when any of groups $R^1$ and $R^2$ is not said group -E-F, said remaining groups $R^1$ or $R^2$ are selected from hydrogen, $C_1$-$C_6$ alkyl, benzyl, mono- or di-nitro-substituted benzyl and —$(CH_2)_k$—W;

wherein W is selected from sulphonate, sulphonic acid, quaternary ammonium and carboxyl; and k is an integer from 1 to 6.

2. A reagent for luminescent detection of a target material wherein said reagent includes the dye of claim 1 wherein none of groups $R^1$, $R^2$, $R^3$, $R^4$, $R^5$ and $R^6$ contains a nitro, or mono- or di-nitro substituted benzyl group.

3. The dye of claim 1 wherein at least one of groups $R^1$, $R^2$, $R^3$, $R^4$, $R^5$ and $R^6$ includes at least one nitro group.

4. The dye of claim 1 wherein X and Y are selected from the group consisting of bis-$C_1$-$C_4$ alkyl-substituted carbon, oxygen and sulphur.

5. The dye of claim 1 wherein $Z^1$ and $Z^2$ are selected from the group consisting of phenyl, pyridinyl, naphthyl, quinolinyl and indolyl moieties.

6. The dye of claim 1 wherein said spacer group E is selected from the group consisting of:
—$(CHR')_p$—;
—$\{(CHR')_q$—O—$(CHR')_r\}_s$—;
—$\{(CHR')_q$—NR'—$(CHR')_r\}_s$—;
—$\{(CHR')_q$—(CH=CH)—$(CHR')_r\}_s$—; and
—$\{(CHR')_q$—CO—NR'—$(CHR')_r\}_s$— where R' is hydrogen or $C_1$-$C_4$ alkyl, p is 1–20, preferably 1–10, q is 0–10, r is 1–10 and s is 1 or 2.

7. The dye of claim 1 wherein at least one of the groups $R^1$, $R^2$, $R^3$, $R^4$, $R^5$, $R^6$, $R^8$, and $R^9$ includes a water solubilising group.

8. The dye of claim 7 wherein said water solubilising group(s) are selected from the group consisting of sulphonate, sulphonic acid and quaternary ammonium attached directly to the aromatic ring structures $Z^1$ and/or $Z^2$.

9. The dye of claim 7 wherein at least one of groups $R^1$, $R^2$, $R^3$, $R^4$, $R^5$, $R^6$, $R^8$, and $R^9$ includes the group —$(CH_2)_k$—W where W is selected from the group consisting of sulphonate, sulphonic acid, quaternary ammonium and carboxyl; and k is an integer from 1 to 6.

10. The dye of claim 1 wherein $R^7$ is meso-substituted —CN and any remaining groups $r^7$ are hydrogen.

11. A method for labelling a target biological material comprising:
i) adding to a liquid containing said target material a fluorescent dye of formula (1):

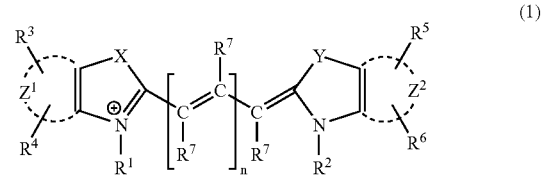

wherein:
groups $R^3$ and $R^4$ are attached to the $Z^1$ ring structure and groups $R^5$ and $R^6$ are attached to the $Z^2$ ring structure, and n=1, 2 or 3;

$Z^1$ and $Z^2$ independently represent the atoms necessary to complete one ring, or two fused ring aromatic or heteroaromatic systems, each ring having five or six atoms selected from carbon atoms and optionally no more than two atoms selected from oxygen, nitrogen and sulphur;

X and Y are the same or different and are selected from oxygen, sulphur, —CH=CH— and the group:

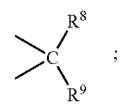

at least one of groups $R^1$, $R^2$, $R^3$, $R^4$, $R^5$, $R^6$ (and $R^8$ and $R^9$ if present) is the group -E-F where E is a spacer group having a chain from 1–20 atoms selected from the group consisting of carbon, nitrogen, oxygen, sulphur and phosphorus atoms and F is a target bonding group;

one of groups $R^7$ is selected from —CN and —$CF_3$;

remaining groups $R^7$ are hydrogen or two of $R^7$ together with the group:

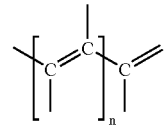

form a hydrocarbon ring system which may optionally contain a heteroatom selected from —O—, —S—, or >NH and n is hereinbefore defined;

when any of groups $R^3$, $R^4$, $R^5$ and $R^6$ is not said group -E-F, said remaining groups $R^3$, $R^4$, $R^5$ and $R^6$ are independently selected from hydrogen, halogen, hydroxyl, amino, mono- or di-$C_1$-$C_4$ alkyl-substituted amino, sulphydryl, carboxyl, $C_1$-$C_6$ alkoxy, $C_1$-$C_6$ alkyl, aryl, heteroaryl, aralkyl, sulphonate, sulphonic acid, quaternary ammonium and the group —$(CH_2)_k$—W;

when any of groups $R^8$ and $R^9$ is not said group -E-F, said remaining groups $R^8$ or $R^9$ are independently selected from $C_1$-$C_4$ alkyl and —$(CH_2)_k$—W;

when any of groups $R^1$ and $R^2$ is not said group -E-F, said remaining groups $R^1$ or $R^2$ are selected from hydrogen, $C_1$-$C_6$ alkyl, benzyl and —$(CH_2)_k$—W;

wherein W is selected from sulphonate, sulphonic acid, quaternary ammonium and carboxyl; and k is an integer from 1 to 6; and ii) incubating said fluorescent dye with said target material under conditions suitable for binding to and thereby labelling said material.

12. The method of claim 11 wherein said target biological material is selected from the group consisting of antibody, lipid, protein, peptide, carbohydrate, nucleotides which contain or are derivatized to contain one or more of an amino, sulphydryl, carbonyl, hydroxyl and carboxyl, phosphate and thiophosphate groups, and oxy or deoxy polynucleic acids which contain or are derivatized to contain one or more of an amino, sulphydryl, carbonyl, hydroxyl and carboxyl, phosphate and thiophosphate groups, microbial materials, drugs, hormones, cells, cell membranes and toxins.

13. A method for the assay of an analyte in a sample comprising:
   i) contacting the analyte with a specific binding partner for said analyte under conditions suitable to cause the binding of at least a portion of said analyte to said specific binding partner to form a complex and wherein one of said analyte and said specific binding partner is labelled with a fluorescent dye of formula (1):

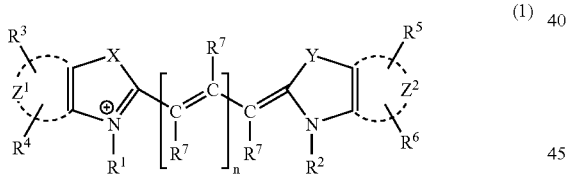

wherein:
   groups $R^3$ and $R^4$ are attached to the $Z^1$ ring structure and groups $R^5$ and $R^6$ are attached to the $Z^2$ ring structure, and n=1, 2 or 3;
   $Z^1$ and $Z^2$ independently represent the atoms necessary to complete one ring, or two fused ring aromatic or heteroaromatic systems, each ring having five or six atoms selected from carbon atoms and optionally no more than two atoms selected from oxygen, nitrogen and sulphur;
   X and Y are the same or different and are selected from oxygen, sulphur, —CH═CH— and the group:

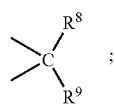

at least one of groups $R^1$, $R^2$, $R^3$, $R^4$, $R^5$, $R^6$ (and $R^8$ and $R^9$ if present) is the group -E-F where E is a spacer group having a chain from 1–20 atoms selected from the group consisting of carbon, nitrogen, oxygen, sulphur and phosphorus atoms and F is a target bonding group;

one of groups $R^7$ is selected from —CN and —$CF_3$;

remaining groups $R^7$ are hydrogen or two of $R^7$ together with the group:

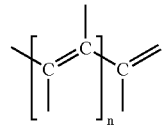

form a hydrocarbon ring system which may optionally contain a heteroatom selected from —O—, —S—, or >NH and n is hereinbefore defined;

when any of groups $R^3$, $R^4$, $R^5$ and $R^6$ is not said group -E-F, said remaining groups $R^3$, $R^4$, $R^5$ and $R^6$ are independently selected from hydrogen, halogen, hydroxyl, amino, mono- or di-$C_1$-$C_4$ alkyl-substituted amino, sulphydryl, carboxyl, $C_1$-$C_6$ alkoxy, $C_1$-$C_6$ alkyl, aryl, heteroaryl, aralkyl, sulphonate, sulphonic acid, quaternary ammonium and the group —$(CH_2)_k$—W;

when any of groups $R^8$ and $R^9$ is not said group -E-F, said remaining groups $R^8$ or $R^9$ are independently selected from $C_1$-$C_4$ alkyl and —$(CH_2)_k$—W;

when any of groups $R^1$ and $R^2$ is not said group -E-F, said remaining groups $R^1$ or $R^2$ are selected from hydrogen, $C_1$-$C_6$ alkyl, benzyl and —$(CH_2)_k$—W;

wherein W is selected from sulphonate, sulphonic acid, quaternary ammonium and carboxyl; and k is an integer from 1 to 6;

ii) measuring the emitted fluorescence of the labelled complex; and iii) correlating the emitted fluorescence with the presence or the amount of said analyte in said sample.

14. The method of claim 13 wherein said analyte-specific binding partner pairs are selected from the group consisting of antibodies/antigens, lectins/glycoproteins, biotin/streptavidin, hormone/receptor, enzyme/substrate and co-factor, DNA/DNA, DNA/RNA and DNA/binding protein.

15. A set of two or more different fluorescent dyes comprising at least one dye of formula (1):

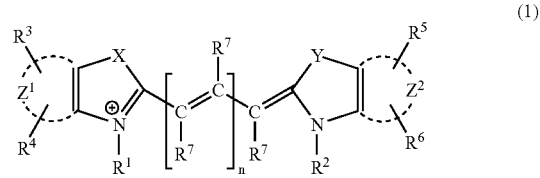

wherein:
   groups $R^3$ and $R^4$ are attached to the $Z^1$ ring structure and groups $R^5$ and $R^6$ are attached to the $Z^2$ ring structure, and n=1, 2 or 3;
   $Z^1$ and $Z^2$ independently represent the atoms necessary to complete one ring, or two fused ring aromatic or heteroaromatic systems, each ring having five or six atoms selected from carbon atoms and optionally no more than two atoms selected from oxygen, nitrogen and sulphur;

X and Y are the same or different and are selected from oxygen, sulphur, —CH═CH— and the group:

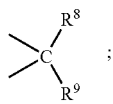

at least one of groups $R^1$, $R^2$, $R^3$, $R^4$, $R^5$, $R^6$ (and $R^8$ and $R^9$ if present) is the group -E-F where E is a spacer group having a chain from 1–20 atoms selected from the group consisting of carbon, nitrogen, oxygen, sulphur and phosphorus atoms and F is a target bonding group;

one of groups $R^7$ is selected from —CN and —$CF_3$;

remaining groups $R^7$ are hydrogen or two of $R^7$ together with the group:

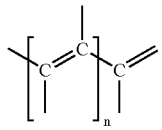

form a hydrocarbon ring system which may optionally contain a heteroatom selected from —O—, —S—, or >NH and n is hereinbefore defined;

when any of groups $R^3$, $R^4$, $R^5$ and $R^6$ is not said group -E-F, said remaining groups $R^3$, $R^4$, $R^5$ and $R^6$ are independently selected from hydrogen, halogen, hydroxyl, amino, mono- or di-$C_1$–$C_4$ alkyl-substituted amino, sulphydryl, carboxyl, $C_1$–$C_6$ alkoxy, $C_1$–$C_6$ alkyl, aryl, heteroaryl, aralkyl, sulphonate, sulphonic acid, quaternary ammonium and the group —$(CH_2)_k$—W;

when any of groups $R^8$ and $R^9$ is not said group -E-F, said remaining groups $R^8$ or $R^9$ are independently selected from $C_1$–$C_4$ alkyl and —$(CH_2)_k$—W;

when any of groups $R^1$ and $R^2$ is not said group -E-F, said remaining groups $R^1$ or $R^2$ are selected from hydrogen, $C_1$–$C_6$ alkyl, benzyl and —$(CH_2)_k$—W;

wherein W is selected from sulphonate, sulphonic acid, quaternary ammonium and carboxyl; and k is an integer from 1 to 6; and wherein each dye of said set has a distinguishably different fluorescence emission wavelength compared with the emission wavelengths of the remaining dyes of the set.

16. The set of claim 15 including four different dyes, each dye of the set having a different fluorescence emission wavelength.

17. An assay method comprising:
i) separating two components which are in an energy transfer relationship, the first component being labelled with a fluorescent donor dye of claim 1 wherein none of groups $R^1$, $R^2$, $R^3$, $R^4$, $R^5$ and $R^6$ contains a nitro, or mono- or di-nitro substituted benzyl group and the second component being labelled with an acceptor dye of claim 1 wherein at least one of groups $R^1$, $R^2$, $R^3$, $R^4$, $R^5$ and $R^6$ includes at least one nitro group; and
ii) detecting the presence of the first component by measuring emitted fluorescence.

18. An assay method comprising:
i) binding one component of a specific binding pair with a second component of said pair, said first component being labelled with a fluorescent donor dye of claim 1 wherein none of groups $R^1$, $R^2$, $R^3$, $R^4$, $R^5$ and $R^6$ contains a nitro, or mono- or di-nitro substituted benzyl group and said second component being labelled with an acceptor dye of claim 1 wherein at least one of groups $R^1$, $R^2$, $R^3$, $R^4$, $R^5$ and $R^6$ includes at least one nitro group; so as to bring about an energy transfer relationship between said first and second components; and,
ii) detecting the binding of the first and second components by measuring emitted fluorescence.

19. An assay method comprising:
separating two components which are in an energy transfer relationship, the first component being labelled with a fluorescent donor dye selected from the group consisting of fluorescein, rhodamine, cyanine dyes and derivatives of bis-pyrromethine boron difluoride dyes and the second component being labelled with a non-fluorescent or substantially non-fluorescent acceptor dye of claim 1 wherein at least one of groups $R^1$, $R^2$, $R^3$, $R^4$, $R^5$ and $R^6$ comprises at least one nitro group; and
ii) detecting the presence of the first component by measuring emitted fluorescence.

20. An assay method comprising:
binding one component of a specific binding pair with a second component of said pair, said first component being labelled with a fluorescent donor dye selected from the group consisting of fluorescein, rhodamine, cyanine dyes and derivatives of bis-pyrromethine boron difluoride dyes and said second component being labelled with a non-fluorescent or substantially non-fluorescent acceptor dye of claim 1 wherein at least one of groups $R^1$, $R^2$, $R^3$, $R^4$, $R^5$ and $R^6$ comprises at least one nitro group; so as to bring about an energy transfer relationship between said first and second components; and
ii) detecting the binding of the first and second components by measuring emitted fluorescence.

* * * * *